United States Patent [19]

Cushing

[11] 3,948,744
[45] Apr. 6, 1976

[54] FLUSH MOUNTED CORROSION ELECTRODE
[75] Inventor: Ralph H. Cushing, Omaha, Nebr.
[73] Assignee: Northern Natural Gas Company, Omaha, Nebr.
[22] Filed: Jan. 2, 1975
[21] Appl. No.: 537,840

[52] U.S. Cl............... 204/195 C; 23/253 C; 73/86; 324/29; 324/65 CR; 324/71 R; 204/280; 204/286; 204/297 R
[51] Int. Cl.² ................ G01N 27/30; G01N 27/08
[58] Field of Search........ 204/1 T, 195 C, 280, 286, 204/297 R, 1 C; 324/29, 65 CR, 71 R; 73/86; 23/253 C

[56] References Cited
UNITED STATES PATENTS

| | | | |
|---|---|---|---|
| 3,087,506 | 4/1963 | Seffens | 324/65 CRP X |
| 3,166,485 | 1/1965 | Lloyd | 204/1 T |
| 3,320,570 | 5/1967 | Lied, Jr. | 324/65 CRP X |
| 3,486,996 | 12/1969 | Annand | 204/195 C |
| 3,488,274 | 1/1970 | Geld | 204/196 |
| 3,846,795 | 11/1974 | Jones | 340/421 |
| 3,910,830 | 10/1975 | Mayse | 204/195 C |

OTHER PUBLICATIONS
"Handbook of Corrosion Testing & Evaluation," edited by W. H. Ailor, Wiley, N.Y. (1971), pp. 603–605.

Primary Examiner—John H. Mack
Assistant Examiner—Aaron Weisstuch
Attorney, Agent, or Firm—Donald F. Haas

[57] ABSTRACT

An electrode useful in measuring rate of corrosion at the inside surface of a conduit containing a corrosive atmosphere is designed to be inserted in the wall of the conduit and mounted flush with its inside surface. The electrode is formed of three pieces: an elongated cylindrical metallic conductor, a cylindrical metallic tip, and a threaded screw. The tip is shaped such that when the electrode is inserted within the wall of the conduit, the shaped surface of the tip can be positioned exactly flush with the inside surface thereof.

An electrode holder is inserted into a hole cut in the conduit and held in place by a welded reinforcing plate on the outside surface of the conduit. An electrode is inserted within the holder and held in place by a retainer cap. When the electrode is to be removed, the retainer cap is taken off and the electrode stays in place by virtue of the frictional forces between it and an elastomeric sleeve which is in place between the electrode and the electrode holder. A portable ball valve is attached to the electrode holder to prevent escape of the conduit's contents. A retraction tool is inserted through the blocking valve, attached to the electrode, and removed, taking the electrode with it.

5 Claims, 4 Drawing Figures

FLUSH MOUNTED CORROSION ELECTRODE

BACKGROUND OF THE INVENTION

This invention relates to measuring and testing corrosion processes and it particularly relates to an improved corrosion electrode for such use.

It is often desirable to determine the rates at which metals corrode within a corrodent. For example, corrosion inhibitors are added to corrosive liquids to reduce the corrosion of exposed metals. Instruments are used to measure the rates at which these metals corrode so that the effectiveness of the inhibitor can be determined. One known method for determining rate of corrosion consists of placing a metal coupon or test specimen in a position where it is exposed to the corrosive atmosphere being studied and connecting it in an electrical circuit so that the electrical resistance of the coupon can be observed. The corroding coupon is then compared with a similar coupon placed in a protected atmosphere. The theory behind this method is that the change in electrical resistance and the change in cross-sectional area of the coupon are proportional and thus can be used to determine the rate of corrosion.

U.S. Pat. Nos. 2,856,495 to Chittum, Whittier and Armstrong, and 2,864,252 to Schaschl utilize the above method. However, the accuracy of this method depends upon the theoretical assumption that the cross-sectional area of the coupon decreases uniformly as the coupon corrodes. This is not a good assumption for many metals as they will tend to form pits (i.e., small crevices) which will fill up with metal oxides and liquid. The electrical resistance across these areas could just as well be higher or the same, as well as lower, after the metal is corroded.

To get around this problem, a new method was devised as discussed in U.S. Pat. 3,661,750 to Wilson. The measurement of the rate of corrosion upon metals by this technique utilizes an instrument associated with a probe carrying metallic electrodes. The probe and electrodes are immersed in the corrodent. The electrodes in the corrodent undergo certain electro-chemical changes that are related to the corrosion of the specimen metal of which the test electrode is formed. The rate of corrosion can be correlated with the electro-chemical effects upon the metallic test electrode contacted by the corrodent. The corrosion of metallic materials by a corrodent causes the production of electrical energy by electro-chemical action. For example, two metallic electodes immersed in a corrodent develop a potential difference as a result of half-cell effects. The potential in a freely corroding test electrode (no external current application) in a dynamic system where the corrodent products are either diffusing or dissolving, eventually reaches a certain steady-state potential differential relative to a reference electrode. This potential difference may be termed the freely corroding potential of the metallic test electrode forming the half-cell subjected to the corroding environment.

An improvement in the above system has been the use of a third electrode. With the three electrode system, the reference electrode provides a measure of the freely corroding potential developed in the electrolyte. At periodic intervals, a separate auxiliary electrode is activated by introducing a potential 10mv higher than that measured between the test and reference electrodes. Under these conditions it has been found that the current flowing between the auxiliary and test electrodes is linearly correlatable to the corrosion rate of the electrode material in the electrolyte. This is due to the fact that (1) the small impressed voltage across the electrodes for short periods of time does not produce permanent polarization of the electrode surfaces, and (2) the major resistance in the circuit is the resistance of the film formed at the interface between the electrode and the electrolyte. Any change in the composition of the electrolyte or its corrosivity, vis-a-vis, the material of the electrode is instantaneously reflected in changes in the resistance of this film which is detected directly in a change in the current flow in the circuit. The theory on which these facts are based is discussed in detail in M. Stern and A. L. Geary, Journal of the Electrochemical Society, 104, 56 (1957).

In the past, the probes carrying metallic electrodes as described above have been placed at the inside wall perpendicular to the flow or within the flow and parallel to it. This kind of positioning causes certain inaccuracies in the corrosion rate measurement. In the case of probes placed perpendicular to the flow, inaccuracies are produced by: the turbulence caused by the probe and the electrodes protruding from it, shielding of the electrodes from the flow of the electrolyte by the adjacent electrodes, the uncertain longitudinal velocity profile across the electrodes, and the unknown horizontal velocity profile across the cylindrical surfaces of the electrodes. In the case of probes placed parallel to the flow, inaccuracies are caused by: deposits of oxides, etc., at the base of the electrodes between the holder and the electrodes, formation of air pockets at the base of the electrodes when the oxygen concentration in the flowing stream is large, and the uneven nature of the film thickness due to turbulence at the edges of the electrodes. Most of these problems can be solved by placing a cigar shaped probe parallel to the flow. The electrodes on this probe are bands wrapped around the probe which do not cause the turbulence problem that the protruding electrodes do. However, these electrodes cannot be removed for individual weighing or examination without total destruction of the probe holder.

The flush mounted electrodes of the present invention eliminate all of the above problems. Thus, accurate measurements of the corrosion rate can be made using an easily removable and relatively inexpensive electrode.

SUMMARY OF THE INVENTION

Briefly, the present invention is an electrode which is adapted to be inserted within the wall of a conduit such as a pipe which contains a corrosive atmosphere to be used in measuring the corrosion current at the inside surface thereof. The electrode is comprised of a metallic conductor having a threaded aperture at one end and a section of reduced diameter at its other end. This section has means on it for attachment to a tool for insertion of said electrode within and retraction of said electrode from the wall of the conduit and also has means protruding from it for making an electrical connection. A removable metallic tip is secured to the conductor by a threaded male member protruding from one end of the tip which is adapted to fit snugly within the aperture in the conductor. The surface contour of the other end of the tip is shaped such that when the electrode is inserted within the wall of the conduit, the shaped surface of the tip can be positioned exactly flush with the inside surface thereof to assist in accurate measurement of the corrosion current thereat.

In an alternative embodiment, the edges of the shaped surface of the tip are rounded such that a small tapered crevice is formed between the tip and the inside surface of the conduit to simulate pitting and/or crevice corrosion. In either embodiment, the attachment means may comprise a pair of lugs protruding from the side surface of the conductor's section of reduced diameter. The lugs are adapted for engagement with lug notches on an insertion and retraction tool. Obviously, the lugs are not essential to the invention and many other methods for engaging the tool could be used.

DESCRIPTION OF THE PREFERRED EMBODIMENTS

Figure 1:
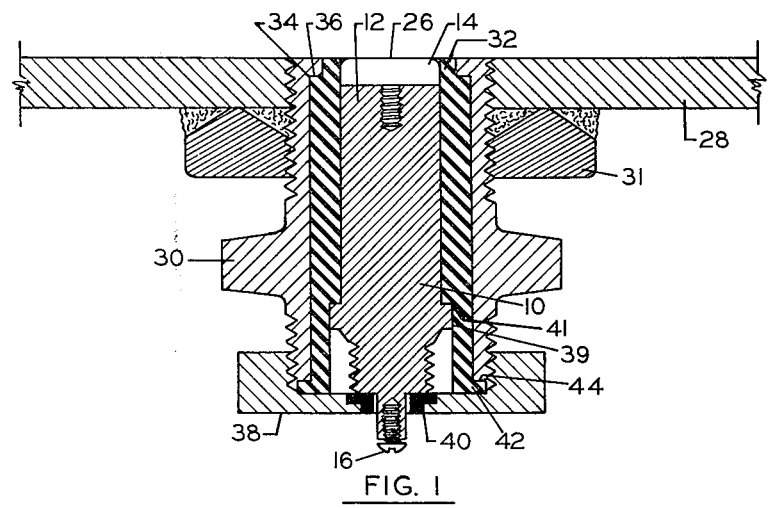
FIG. 1 is a cross-sectional view of an electrode in corrosion rate-measuring position within the electrode holder.
Figure 2:
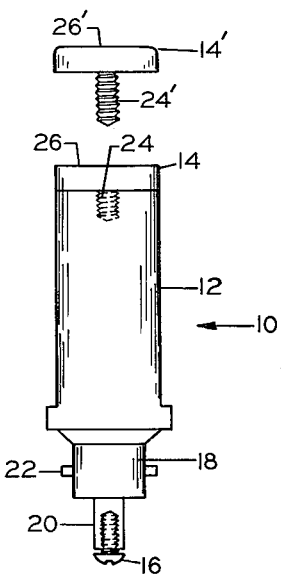
FIG. 2 is a plan view of an electrode showing both the preferred and optional tips.

FIGS. 1 and 2 illustrate the construction and positioning of the electrode 10. The electrode 10 is comprised of an elongated cylindrical metallic conductor 12 having threaded apertures at each of its ends, a removable flattened cylindrical metallic tip 14 for the conductor 12, and an electrical connection screw 16. The conductor 12 has two sections 18, 20 of reduced diameter at one end thereof.

The first section 18 has a reduced diameter to allow insertion of and attachment to an insertion and retraction tool. Said section 18 also has lugs 22 for attachment to such tool. In FIG. 1, an alternative embodiment is shown wherein the lugs are replaced by threads on the section 18. The second section 20 of reduced diameter holds the electrical connection screw 16 which is threadably mounted in the aperture at the end of the section 20.

Figure 3:
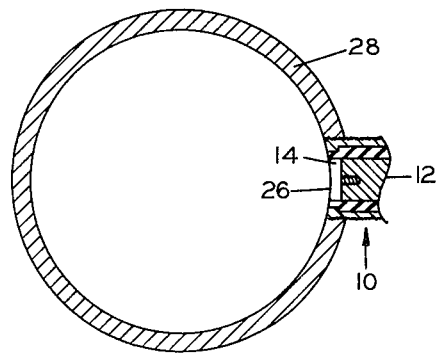
FIG. 3 is cut-off view of a portion of FIG. 1 illustrating the flush positioning of the electrode tip.

The metallic tip 14 has a threaded male member 24' at one end thereof for threadably mounting the tip 14 in the other aperture in the conductor 12. The opposite end 26 of the tip 14 is shaped to correspond exactly with the curvature of the inside wall of the conduit 28 into which the electrode 10 is inserted. Flush positioning of the active surface of the electrode 10, i.e., shaped end 26 of the tip 14, with the inside wall of the conduit 28 is the major advantage of the present invention and eliminates the problems discussed above because there is no interruption of the flow within the conduit 28. This is illustrated by FIG. 3. An optional tip 14' has rounded edges to form small tapered crevices between the tip and the wall of the conduit 28 to simulate and study pitting and/or crevice corrosion.

The electrode 10 of this invention can be made and the advantages discussed above can be obtained without a tip 14, but the tip 14 itself is very advantageous. The tip 14 provides an easy, inexpensive way to examine the effects of corrosion and to determine the amount of corrosion by the change in weight of the tip 14 without having to replace the entire electrode 10. Furthermore, a great number of tips can be made of different metals and into different shapes to be used with one conductor 12.

The electrode 10 is mounted in a hollow cylindrical electrode holder 30 (see FIG. 1) which is threadably mounted in the wall of the conduit 28 and positioned so as to be exactly flush with the inside wall of the conduit 28. One end of the holder 30 must be shaped to conform with the curvature of the inside wall of the conduit 28. A welded reinforcing plate 31 helps to secure the holder 30. A hollow cylindrical elastomeric insulating sleeve 32 is inserted within the holder 30 so that it fits snugly against the walls thereof. A shoulder 34 on the sleeve 32 engages a shoulder 36 on the holder 30 to prevent the sleeve 32 from protruding into the conduit 28. When it is not compressed, the thickness of the sleeve 32 narrows in the direction of the conduit 28. When the electrode 10 is positioned within the holder 30, the sleeve 32 is compressed to the regular shape as illustrated in FIG. 1. The sleeve 32 is attached to the electrode 10 using adhesives or, alternatively, mechanical ridges built into the sleeve 32 and the electrode 10. These hold the sleeve 32 and the electrode 10 in juxtaposition for precise insertion into the electrode holder 30 so nothing protrudes into the conduit 28. The compression and the nature of the elastomeric material create a sufficient frictional force to hold the electrode 10 in place when the retainer cap 38 is removed. This greatly facilitates the insertion and retraction of the electrode 10. In use, the sleeve 32 and the electrode 10 are inserted and removed together. Additionally, annular shoulder 39 on the conductor 12 engages shoulder 41 on the sleeve 32 to help prevent the electrode 10 from protruding into the conduit 28.

The retainer cap 38 is threadably mounted on the holder 30. The cap 38 has an aperture in the center thereof to allow the second section 20 of the conductor 12 and the electrical connection screw 16 to protrude therethrough to allow completion of the electrical circuit necessary to measure the rate of corrosion of the tip 14. An insulating washer 40 provides a seal between the electrode 10 and the cap 38.·

The movement of the cap 38 towards the conduit 28 is restricted by an annular flange 42 on the sleeve 32 which engages edge 44 on the holder 30. The length of the electrode 10 is such that when the cap 38 is screwed on as tight as possible, the shaped end 26 of the tip 14 is positioned exactly flush with the inside wall of the conduit 28. The frictional force between the electrode 10 and the sleeve 32 prevents the electrode 10 from protruding into the conduit 28. Also, the sleeve 32 provides a tight seal between the electrode 10 and the conduit 28.

Figure 4:
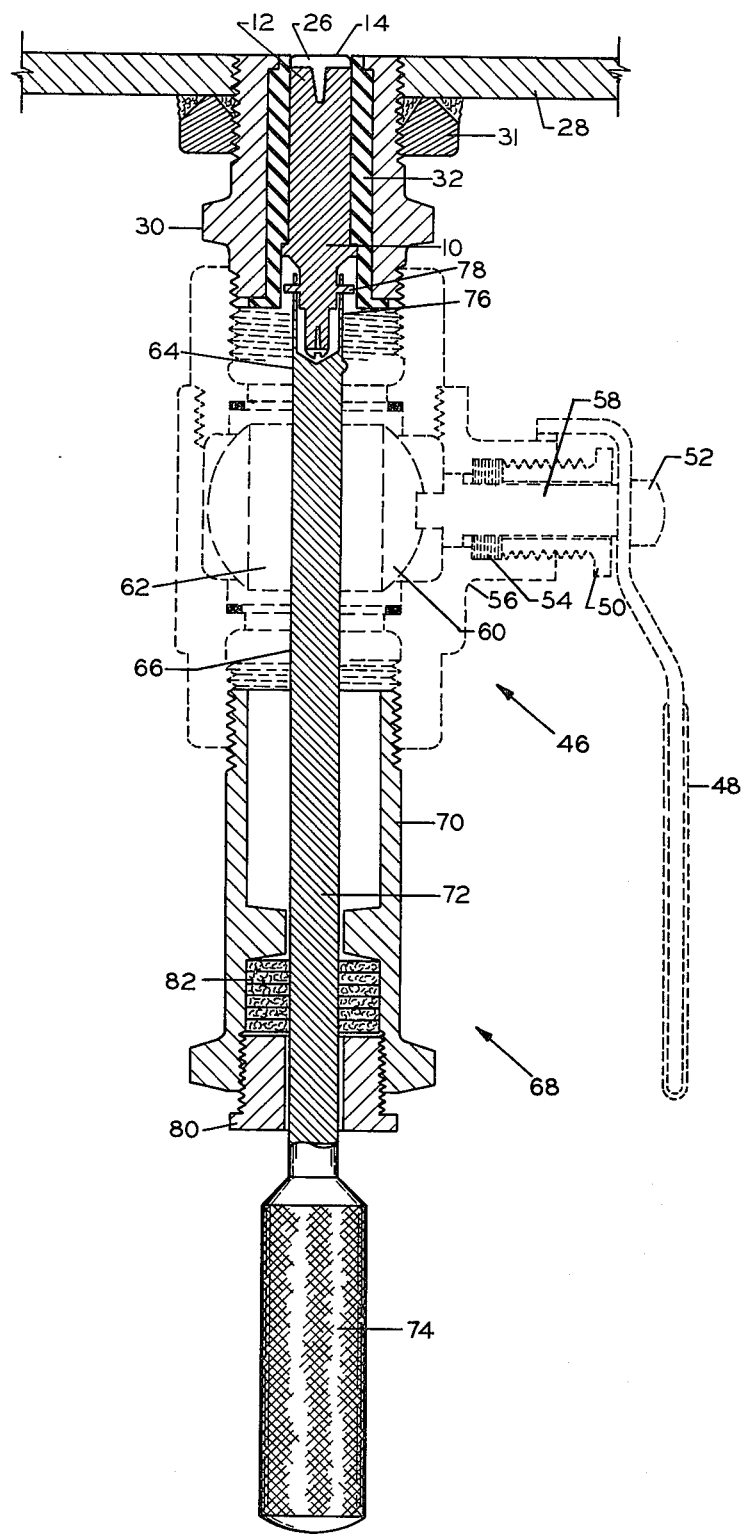
FIG. 4 is a cross-section of the electrode with the blocking valve and the insertion and retraction tool in position for retraction of the electrode.

FIG. 4 illustrates the insertion and retraction of the electrode 10. The retainer cap 38 is removed and a standard ball valve 46 (or any straight-through valve such as gate and plug valves) is threadably mounted on the electrode holder 30. The ball valve 46 has a handle 48 secured on a packing nut 50 by nut 52. Packing 54 is provided between packing nut 50 and the body 56 of the valve 46 to prevent leakage. The nut 52 is threadably mounted on shaft 58 which rotates within the packing nut 50 and is secured to ball 60 such that the ball 60 and the shaft 58 rotate when the handle 48 is rotated. The ball 60 has a cylindrical passage 62 to allow insertion and retraction of the electrode 10, as shown, through smaller cylindrical passages 64, 66 in the valve body 56. When the ball 60 is rotated, any conduit fluid present in the first valve body passage 64 is prevented from flowing to the second valve body passage 66.

The insertion and retraction tool 68 is comprised of a hollow body portion 70, which is threadably mounted on the ball valve 46, and an elongated cylindrical rod 72 which fits within valve body passages 64, 66 such that no conduit fluid can escape through the passages 64, 66. The rod 72 has a handle 74 at one end and is hollow at the other to accommodate the second section 20 of the conductor 12. The hollow end 76 of the rod 72 has lug notches 78 within it. Packing nut 80 and packing 82 prevent leaking.

The rod 72 is inserted through hollow tool body 70 into the valve body passages 64, 66 and the ball passage 62. The lug notches 78 within the hollow end 76 engage the lugs 22 on the conductor 12 and then the electrode 10 is removed with the rod 72. When electrode 10 passes the ball 60, the ball valve handle 48 is rotated to halt the flow of conduit fluid. Then the electrode 10 can be taken out, the tip 14 can be changed, and the electrode 10 can be replaced, all within a very short period of time with surprisingly little effort and expense.

I claim:

1. An electrode assembly contained within the wall of a conduit which contains a corrosive atmosphere for use in measuring the corrosion current at the inside surface of the conduit, said electrode assembly comprising:
   a. An electrode comprising a metallic conductor having a threaded aperture at one end and a section of reduced diameter at its other end, said section having means thereon for attachment to a tool for insertion of said electrode within and retraction of said electrode from the wall of the conduit and means protruding therefrom for making an electrical connection; and a removable metallic tip having a threaded male member protruding from one end thereof and adapted to fit snugly within said aperture to secure said tip to said conductor, and having the surface contour of the other end of said tip shaped such that when said electrode is inserted within the wall of the conduit, said shaped surface of said tip can be positioned exactly flush with the inside surface of the conduit for accurate measurement of the corrosion current thereat;
   b. Hollow cylindrical holding means open at both ends and mounted within an opening in said conduit for positioning said electrode within said holding means such that said shaped surface of said tip is positioned exactly flush with the inside surface of said conduit; and
   c. Retaining means for retaining said electrode in said flushmounted position, said retaining means being detachably mounted on the end of said holding means opposite from said conduit.

2. An electrode assembly as defined in claim 1 and further characterized in that the edges of said shaped surface of said tip are rounded such that a small tapered crevice is formed between said tip and said inside surface of said conduit to simulate pitting and crevice corrosion.

3. An electrode assembly as defined in claim 1 and further characterized in that said attachment means comprises a pair of lugs protruding from the side surface of said section of reduced diameter, said lugs adapted for engagement with lug notches on an insertion and retraction tool.

4. An electrode assembly as defined in claim 1 and further characterized in that said attachment means comprises threads on said section of reduced diameter, said threads adapted for engagement with threads on an insertion and retraction tool.

5. An electrode assembly as defined in claim 1 and further characterized in that a cylindrical elastomeric sleeve surrounds said electrode and is adhesively attached thereto, whereby said electrode is positioned exactly flush with the inside surface of the conduit, a tight seal is provided between said electrode and said conduit, and sufficient friction is provided to hold said electrode in place within said holding means under moderate pressure when said retaining means is detached.

* * * * *